United States Patent
Tanaka et al.

[11] Patent Number: 6,159,190
[45] Date of Patent: Dec. 12, 2000

[54] ABSORBENT ARTICLE

[75] Inventors: Masahito Tanaka; Mitsugu Hamajima; Yoji Kameo; Takao Nakayama, all of Tochigi-ken, Japan

[73] Assignee: KAO Corporation, Tokyo, Japan

[21] Appl. No.: 09/136,404

[22] Filed: Aug. 19, 1998

[30] Foreign Application Priority Data

Aug. 29, 1997 [JP] Japan .................................. 9-234712

[51] Int. Cl.⁷ .................................................. A61F 13/15
[52] U.S. Cl. ........................... 604/385.24; 604/385.28; 604/387
[58] Field of Search .................. 604/358, 385.2, 604/385.1, 389, 386, 385.01, 385.02, 355.21–355.28, 385

[56] References Cited

U.S. PATENT DOCUMENTS

| | | | |
|---|---|---|---|
| 4,695,278 | 9/1987 | Lawson | 604/385 |
| 4,704,116 | 11/1987 | Enloe | 604/385 |
| 4,738,677 | 4/1988 | Foreman | 604/385 |
| 4,795,454 | 1/1989 | Dragoo | 604/385.2 |
| 4,808,177 | 2/1989 | DesMarais et al. | 604/385.1 |
| 4,816,025 | 3/1989 | Foreman | 604/385.2 |
| 4,846,825 | 7/1989 | Enloe et al. | 604/385.1 |
| 5,021,051 | 6/1991 | Hiuke | 604/385.2 |
| 5,476,457 | 12/1995 | Roessler et al. | 604/364 |
| 5,542,941 | 8/1996 | Morita | 604/385.1 |
| 5,601,544 | 2/1997 | Glaug et al. | . |
| 5,643,239 | 7/1997 | Bodford et al. | 604/370 |
| 5,704,928 | 1/1998 | Morita et al. | 604/385.1 |

FOREIGN PATENT DOCUMENTS

| | | |
|---|---|---|
| 0219326A2 | 4/1987 | European Pat. Off. . |
| 0534488A1 | 3/1993 | European Pat. Off. . |
| 0558889A1 | 9/1993 | European Pat. Off. . |
| 297271 | 2/1997 | Taiwan . |
| 9709016 | 3/1997 | WIPO . |
| 9709017 | 3/1997 | WIPO . |

*Primary Examiner*—John G. Weiss
*Assistant Examiner*—Carie Mager
*Attorney, Agent, or Firm*—Birch, Stewart, Kolasch & Birch, LLP

[57] ABSTRACT

An absorbent article including a liquid-retentive absorptive layer formed on a liquid-impermeable, leak-preventive layer in a substantially elongated configuration, the absorbent layer including a liquid-permeable top sheet and a liquid-retentive absorbent member, and the absorbent article is provided longitudinally with left and right opposite side portions containing elastic members which extend in the longitudinal direction thereof, wherein the elastic members are covered with an elastic member-attached sheet provided on an inner surface side of the top sheet.

11 Claims, 2 Drawing Sheets

ABSORBENT ARTICLE

BACKGROUND OF THE INVENTION

1. Field of the Invention

The present invention relates to an absorbent article such as a sanitary napkin or an incontinent pad which renders no adverse effect to the skin of the user due to the oozing-out of an adhesive agent. The absorbent article is also superb in fitness and high in its leak-preventive effect.

2. Description of the Related Art

As an absorbent article such as a sanitary napkin and the like, there has heretofore been widely used one including a liquid-retentive absorptive layer and a liquid impermeable leak-preventive layer and formed in a substantially vertically elongated configuration.

In such an absorbent article, the absorbent layer usually comprises a liquid-permeable top sheet and a liquid-retentive absorbent member. Recently, it has been proposed, in order to enhance the fitness and leak-preventive property, that the elastic members should each be disposed on opposite left and right side edge portions of the absorbent member.

However, since it is the usual practice that the elastic member be adhered to the top sheet and the absorbent member through an adhesive agent directly applied to the elastic member, the conventional absorbent article such as a sanitary napkin and the like provided with such an elastic member has the shortcoming in that the adhesive agent oozes out to the top sheet to reach the surface of the top sheet where the adhesive agent contacts the skin of the wearer. This degrades the comfort of the absorbent article when worn by a user. In a worst case, the adhesive agent even adversely affects the skin of the wearer.

SUMMARY OF THE INVENTION

It is, therefore, an object of the present invention to provide an absorbent article which is superb in fitness and in absorbing ability and which renders no adverse effect to the skin of the wearer.

The present inventors have discovered the fact that an absorbent article comprising an elastic member covered with an elastic member-attached sheet provided with an elastic member can achieve the above object.

The present invention provides an absorbent article including a liquid-retentive absorptive layer and a liquid-impermeable, leak-preventive layer and formed in a substantially vertically elongated configuration wherein the absorbent layer includes a liquid-permeable top sheet and a liquid-retentive absorbent member, and wherein the absorbent article is provided on longitudinal left and right opposite side portions thereof with elastic members extending in the longitudinal direction thereof, such that the elastic members are covered with an elastic member-attached sheet provided on the inner surface side of the top sheet.

The absorbent article of the present invention is superb in fitness and in absorbing ability and renders no adverse effect to the skin of the wearer.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein.

DETAILED DESCRIPTION OF THE PREFERRED EMBODIMENTS

Figure 1:
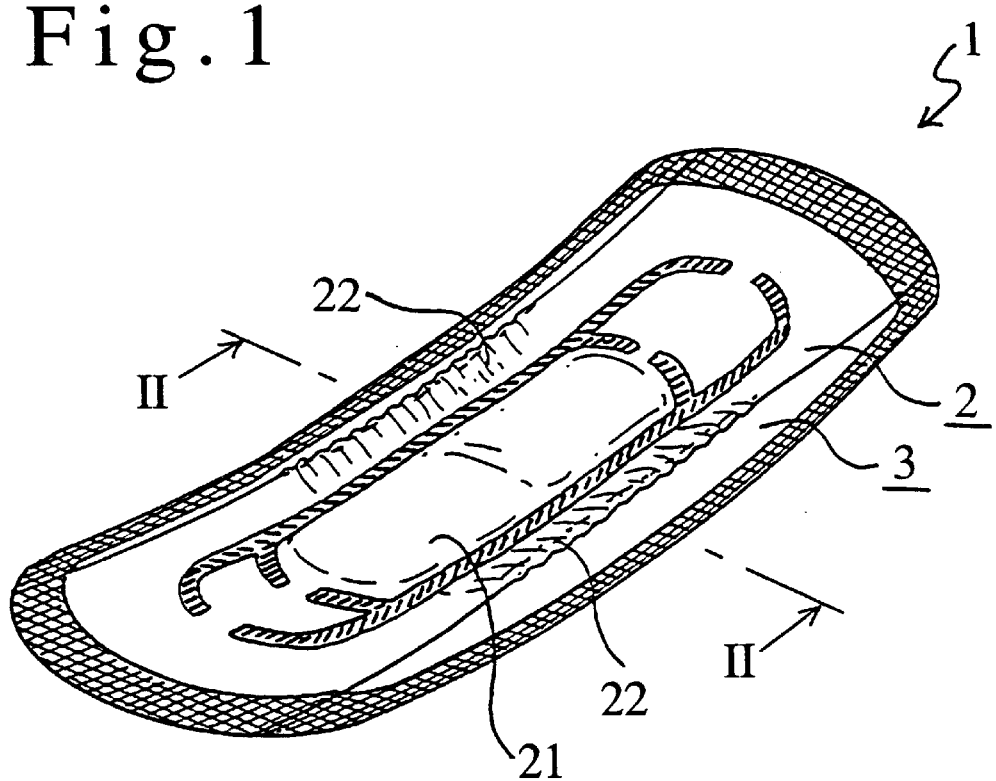
FIG. 1 is a perspective view showing a sanitary napkin as one embodiment of the absorbent article of the present invention.

The absorbent article of the present invention will now be described in detail with reference to the drawing.

Figure 2:
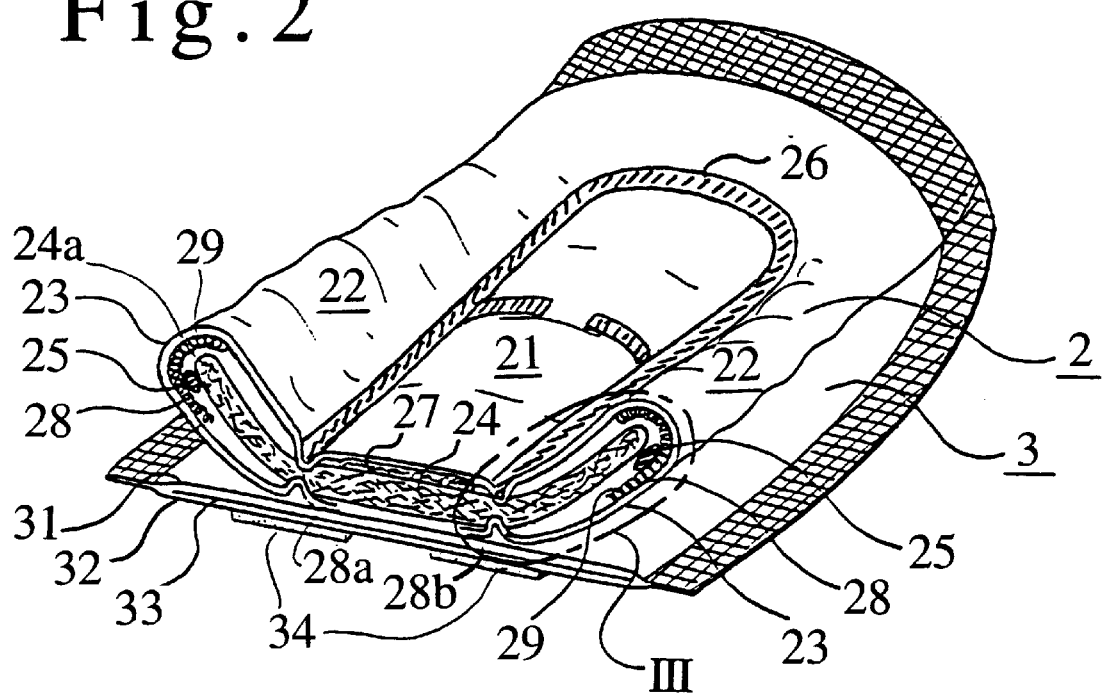
FIG. 2 is a view taken along line II—II of FIG. 1.
Figure 3:
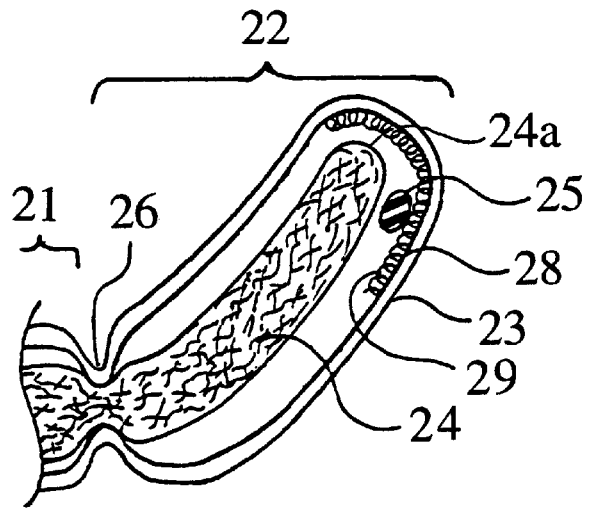
FIG. 3 is an enlarged view of the portion indicated by III of FIG. 2.

FIG. 1 is a perspective view showing a sanitary napkin as one embodiment of the absorbent article of the present invention, and FIG. 2 is a view taken along line II—II of FIG. 1. FIG. 3 is an enlarged view of a portion indicated by III of FIG. 2.

As shown in FIG. 2, a leak-preventive layer 3 comprises a liquid-permeable sheet 31, a leak-preventive sheet 32 and an absorbent core 33 interposed between sheets 31 and 32. That is, the leak-preventive layer 3 is formed by sandwiching an absorbent core 33 composed of an absorptive sheet between the liquid-permeable sheet 31 and the leak-preventive sheet 32, and sealing the liquid-permeable sheet 31 and the leak-preventive sheet 32 at the peripheral edge portions of the absorbent core 33.

An absorptive-layer 2 is placed on the liquid-permeable sheet 31 of the leak-preventive layer 3 and fixed thereto. This fixture is made by adhering left and right opposite side edge portions of the fixture portion 21 with an adhesive agent. The longitudinal opposite end edges of the absorptive-layer 2 and the leak-preventive layer 3 are fixedly heat sealed.

The leak-preventive layer 3 is provided on its back side with an article fixture portion 34 for fixing the sanitary napkin, when in use, to a clothing member such as underwear or any standard undergarment.

In this embodiment, the fixture portion 34 exhibits a strip-like configuration. Two such fixture portions 34 can be provided on the longitudinal left and right opposite side edges of the leak-preventive layer.

As shown in FIGS. 1 and 2, a groove portion 26 is formed at the left and right opposite side edges of the fixture portion 21 so that the above-mentioned free edge portion 22 is more favorably erected or extended in the upward direction.

With regard to the adhesive agent for fixing the liquid-permeable sheet 31, the leak-preventive sheet 32 and the absorptive sheet as the absorbent core 33 constituting the leak-preventive layer 3, the elastic member 25, the absorptive-layer 2, and the viscous agent for forming the article fixture portion 34, any material ordinarily used in an absorbent article such as a sanitary napkin can be used without any particular limitation.

The absorptive-layer 2 includes a liquid-permeable top sheet 23 and a liquid-retentive absorbent member 24. The elastic member 25 is provided on longitudinal left and right opposite side portions of the sanitary napkin 1 along its longitudinal direction such that the elastic member 25 is covered with the top sheet 23 and an elastic member-attached sheet 28 disposed on the inner side (absorbent member side 24) of the top sheet 23.

More specifically, the elastic member 25 is interposed between the absorbent member 24 and the top sheet 23 disposed in such a manner as to cover the absorbent member 24.

The elastic member 25 is fixed to the elastic member-attached sheet 28 through an adhesive agent 29.

The elastic member-attached sheet 28 is disposed in such a manner as to cover the absorbent member 24.

It should be noted that the elastic member-attached sheet 28 is not required to cover the entire absorbent member 24, but it may cover only a part of the absorbent member 24 as long as the effect of attachment of the elastic member 25 can be obtained, and the elastic member 25 can be attached in such a manner that the adhesive agent will not ooze out.

As shown in FIGS. 2 and 3, in the sanitary napkin 1 according to this embodiment, the absorptive-layer 2 is divided into the fixture portion 21 fixed to the leak-preventive layer 3 located on its widthwise central portion, and a pair of left and right free edge portions 22 located widthwise and extending outwardly of the fixture portion 21. The free edge portions 22 form lateral side portions of the fixture portion 21 which are extensions of the fixture portion, since the absorbent member 24 extends into the free edge portions 22. The liquid-permeable top sheet 23 covers the outer surface of the liquid-retentive absorbent member 24 such that the absorbent member 24 is present widthwise over the entire area of the absorptive-layer 2. The elastic members 25 are disposed on the longitudinal left and right opposite side edge portions 24a of the absorbent member 24 along the longitudinal direction of the absorbent member 24 over a predetermined length thereof The free edge portions 22 in the absorptive-layer 2 are extended upwardly of the leak-preventive layer 3 by contraction of the elastic members 25.

As shown in FIG. 2, the absorptive-layer 2 is covered by the liquid permeable top sheet 23 over its entire area, with the exception of the area abutting with liquid permeable sheet of the leak-preventive layer 3. In the absorptive-layer 2, a second absorbent member 27 is disposed on the fixture portion 21 between the top sheet 23 and the absorbent member 24.

With regard to the material for forming the top sheet 23, any material ordinarily used as a top sheet in an absorbent article such as a sanitary napkin can be used without any particular limitation. Preferably the top sheet 23 is formed of a perforated sheet having a bore share of 4 to 30%, a bore of 0.15 to 1.0 mm and composed of a linear low density polyethylene (L-LDPE), low density polyethylene (LDPE), high density polyethylene (HDPE), polypropylene, ethylene vinyl acetate (EVA), or blended polymers thereof.

In this embodiment, the absorbent member 24 is formed of an ordinary absorptive sheet (not shown).

The elastic member 25 is disposed along an edge portion 24a of the absorbent member 24 on the back side of the absorbent member 24 at the free edge portion 22 and generally over the longitudinal entire area of the absorptive-layer 2. The elastic member 25 exhibits a strip-like configuration and is preferably 2 to 15 mm in width.

With regard to the elastic member 25, any material ordinarily used for an absorbent article can be used without any particular limitation. Particularly preferred are elastic members composed of a foamed member of polyolefins or polyurethanes, or, alternatively, natural rubber can be used as the elastic member 25. The elastic member 25 can take the form of a string, a film, or any planar configured member. In this embodiment, a string-like elastic member is used.

The number of the elastic members is not particularly limited. A plurality of elastic members may be provided instead of one each as in this embodiment.

It is preferable that the elastic force of the elastic member is 100 g or less in stress at 20% expansion.

The elastic member-attached sheets 28 are disposed in such a manner as to cover the elastic member 25 and also cover the front and back sides of the absorbent member 24 at the free edge portions 22. That is, the elastic member 25 is disposed such that one surface of the elastic member 25 contacts the absorbent member 24 and the other surface contacts the elastic member-attached sheets 28.

The elastic member-attached sheets 28 cover the entire surface of the free edge portions 22 such that longitudinal left and right opposite side portions 28a, 28b thereof are located on the widthwise more central side than the groove portion 26.

That is, the elastic member-attached sheets 28 are generally the same in configuration as the top sheet and located at the same position as the top sheet.

With regard to the material for forming the elastic member-attached sheets 28, any material capable of preventing the adhesive agent from oozing out can be used without any particular limitation. However, in case the elastic member attached sheets 28 are disposed in such a manner as to cover the front side (skin-contact surface side) of the absorbent member 24 located on the free edge portions 22 as in this embodiment, they are required to be liquid-permeable sheets. AS sheets usable as material for forming the elastic member-attached sheets 28, any material ordinarily used as a top sheet can be used without any limitation. Examples of such sheets include those obtained by forming a liquid-impermeable film composed of the above-mentioned material in the form of a net using perforated film and a thermoplastic resin, and the below-listed nonwoven fabric. In view of rigidity, nonwoven fabric is preferably used. In this embodiment, the elastic member-attached sheets 28 are each formed of a nonwoven fabric.

Nonwoven fabrics are obtained by twisting or adhering fibers together. Particularly preferable in view of flexibility and the sense of touch and outlook is the so-called dried heat-adhered nonwoven fabric obtained by fixing the fibers together by heat welding.

With regard to the fiber composition of the nonwoven fabric, polyolefins, polyesters, acrylics, polyamides, or the like can be freely used. Particularly, preferable composite fibers of polyethylene/polyesters, polyethylene/ polypropylenes or polyethylene/polyethylenes can be used in view of the sense of touch, outlook and strength.

The basic weight of the nonwoven fabric used as the material for forming the elastic member-attached sheet is preferably 10 to 30 g/m$^2$.

The fineness of the composite fibers of the nonwoven fabric is preferably 1.5 to 15d.

If the elastic member-attached sheets 28 are not disposed in such a manner as to cover the absorbent member 24, for example, in case the absorbent member 24 not being present at the free edge portions 22, an ordinary liquid-impermeable sheet may also be used as the elastic member-attached sheet 28.

The sanitary napkin of this embodiment is such that the adhesive agent used for fixing the elastic members will not ooze out of the surface of the absorptive-layer and therefore the comfort is not degraded, and no adverse effect is given to the skin of the wearer.

For the above reasons, the adhesive agent employed in this embodiment can be selected from a wide range of adhesive agents. Specifically, in the sanitary napkin of this embodiment, the adhesive agent for fixing the elastic member can be freely selected from hot melt viscous agents based on styrene, natural rubber, olefins, polyisobutylene, or the like. Since the adhesive agent of this type rarely oozes out to the top side, the material may be of the type ranging from a low melting point of about 90° C. to a high melting point of about 230° C.

With respect to the basic weight of the coating of the adhesive agent, in the case where the adhesive agent is applied directly to the top material, the upper limit is several g/m², but in this embodiment, the adhesive agent can be applied in a large amount of about several tens of g/m² maximum in order to ensure strength of viscosity.

In order to fix the elastic members 25 to the elastic member-attached sheets 28, the basic weight of the adhesive agent to be applied is effective 3 to 25 g/m² and particularly, preferably 5 to 18 g/m², from the viewpoint of adhesive property and the perception of use of the fixed portion.

As described above, since the absorptive-layer 2 is not fixed directly to undergarments or the like but only through the leak-preventive layer 3, the leak-preventive layer 3 follows the motion of the undergarments, etc. but the absorptive-layer 2 does not, and therefore the effect of motion by the wearer is small. Accordingly, the shape of the absorptive-layer 2 rarely collapses and thus it is superb in fitness. Particularly, in the case where the width of the article fixture portion 34 is larger than the width of the fixture portion 21, a particularly effective result can be exhibited because the ratio of the leak-preventive layer 3 following the motion of the wearer can be greatly reduced. Moreover, since the absorbent member 24 is present up to the wide edges of the absorptive-layer 2, the above arrangement is particularly superior in its side leakage-preventive property.

The sanitary napkin of this embodiment can be manufactured as follows. After the elastic member 25 is adhered to the elastic member-attached sheets 28 through an adhesive agent, the elastic member-attached sheets 28 are disposed in such a manner as to cover the top side of the absorbent member 24 located on the fixture portion and the entire absorbent member 24 located on the free edge portion 22. Then, the entirety is covered with the top sheet 23 to form the absorptive-layer 2. Then, after the leak-preventive layer 3 is formed separately, the absorptive-layer 2 and the leak-preventive layer 3 are fixed together using an adhesive agent.

It should be noted, however, that the present invention is not limited to the above-mentioned manufacturing method.

Another embodiment of the absorbent article of the present invention will now be described with reference to FIG. 4.

Figure 4:
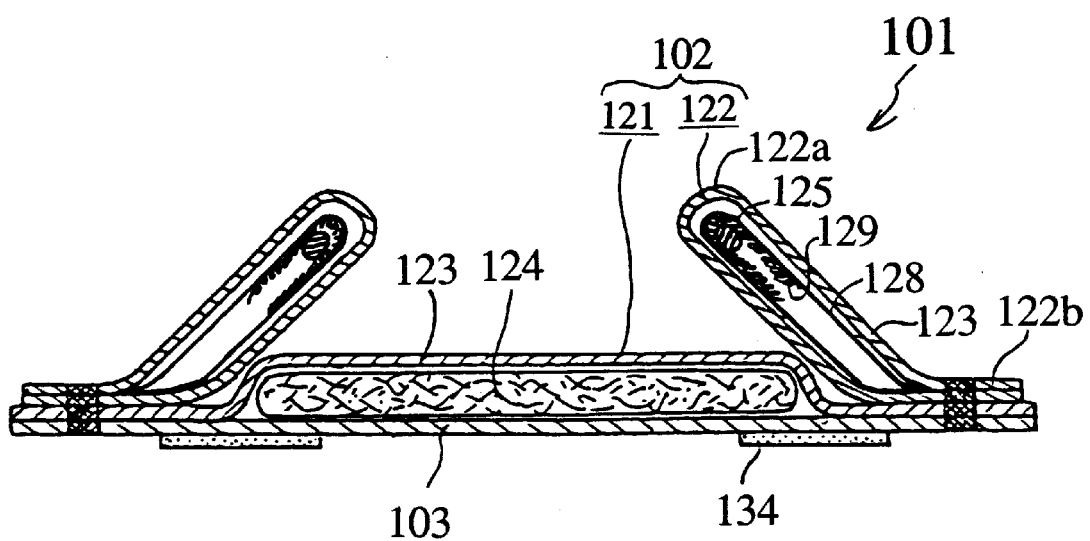
FIG. 4 is a sectional view showing the thickness of the sanitary napkin as another embodiment of the absorbent article of the present invention.

FIG. 4 is a widthwise sectional view showing a sanitary napkin as another embodiment of an absorbent article of the present invention.

In the following description, the reference numeral of each member is the number plus 100 corresponding to each member of the embodiment shown in FIGS. 1 to 3, and elements which are different from the embodiment of FIGS. 1 to 3 are particularly described. The elements not particularly described hereinafter are the same as those of the embodiment shown in FIGS. 1 to 3.

A sanitary napkin 101 as the absorbent article of the embodiment shown in FIG. 4 comprises a fixture portion 121 with an absorptive-layer 102 fixed to a leak-preventive layer 103, and barrier portions 122 fixed such that distal end portions 122a thereof are located on left and right opposite side portions of the fixture portion 121. The barrier portions 122 form lateral side portions of the absorptive-layer 102 which are independent of the fixture portion 121, since the absorbent member 124 is not included in the barrier portions 122.

The fixture portion 121 comprises the absorbent member 124 and the top sheet 123. The barrier portions 122 each comprise a double-folded and hollow-tubular top sheet 123, an elastic member 125 disposed on an inner surface of the top sheet 123 at the distal end portion 122a, and an elastic member-attached sheet 128 disposed in such a manner as to cover the surface of the elastic member 125 between the elastic member 125 and the top sheet 123.

The elastic member 125 is fixed to the elastic member-attached sheet 128 through an adhesive agent 129.

The barrier portions 122 are disposed towards the central portion of the sanitary napkin 101 and erected or extended upwardly and inwardly of the absorbent article by the contraction of the elastic member 125. The barrier portions 122 include opposite side edge portions 122b.

It should be noted that the absorbent article of the present invention is not limited to the above-mentioned embodiments and that a wide range of modifications can be made without departing from the scope of the present invention. For example, in the embodiment of FIGS. 1 to 3, the leak-preventive layer 3 is acceptable even if it does not include the absorbent core 33. The leak-preventive layer 3 may be designed such that the leak-preventive sheet is disposed on the back of the absorbent member and the leak-preventive sheet is covered with the top sheet.

In the embodiment of FIG. 4, the barrier portions 122 may also be disposed in such a manner as to be oriented outwardly of the sanitary napkin 101.

In the absorbent article of the present invention, the whole absorptive layer may be provided with the leak-preventive layer, without dividing the absorptive-layer into the fixture portion 21 and the free edge portions 22.

The invention being thus described, it will be obvious that the same may be varied in many ways. Such variations are not to be regarded as a departure from the spirit and scope of the invention, and all such modifications as would be obvious to one skilled in the art were intended to be included within the scope of the following claims.

What is claimed is:

1. An absorbent article including a liquid-retentive absorptive layer formed on a liquid-impermeable, leak-preventive layer in a substantially elongated configuration, said absorptive layer including a liquid-permeable top sheet and a liquid-retentive absorbent member, wherein said absorbent article is provided on longitudinal left and right opposite side portions thereof with elastic members which extend in the longitudinal direction thereof, said elastic members being covered with an elastic member-attached sheet disposed on the inner surface side of said top sheet, said elastic member-attached sheet being disposed to cover said absorbent member, said elastic member-attached sheet is liquid permeable, said elastic member-attached sheet extending between said absorbent member and said liquid-impermeable, leak preventive layer.

2. The absorbent article according to claim 1, wherein said absorptive layer has a central fixture portion and lateral side portions.

3. The absorbent article according to claim 1, wherein said elastic members are interposed between said absorbent member and said top sheet, said top sheet covering said absorbent member.

4. The absorbent article according to claim 1, wherein said absorbent member is fixed to said elastic member-attached sheet.

5. The absorbent article according to claim 1, wherein said elastic member-attached sheet is formed of a nonwoven fabric.

6. The absorbent article of claim 2, wherein the lateral side portions define left and right free edge portions which extend outwardly and upwardly from a centrally disposed fixture portion due to the contraction of the elastic members.

7. The absorbent article of claim 2, wherein the lateral side portions are extensions of the central fixture portion.

8. The absorbent article according to claim 1, wherein said leak-preventive layer includes a liquid-permeable sheet, a leak-preventive sheet and an absorbent core there between.

9. The absorbent article according to claim 1, wherein said absorptive layer includes a central fixture portion and lateral side portions, said absorbent member extending into said lateral side portions.

10. The absorbent article according to claim 1, wherein said elastic member-attached sheet covers longitudinal left and right opposite side portions of said absorbent member.

11. The absorbent article according to claim 1, wherein said elastic member-attached sheet covers generally an entirety of longitudinal left and right opposite side portions of said absorbent member.

* * * * *